United States Patent [19]

Smith

[11] Patent Number: 4,584,322

[45] Date of Patent: Apr. 22, 1986

[54] PROCESS FOR THE PRODUCTION OF ACETIC ACID FROM SYNTHESIS GAS

[75] Inventor: David W. Smith, Cincinnati, Ohio

[73] Assignee: National Distillers and Chemical Corporation, New York, N.Y.

[21] Appl. No.: 597,984

[22] Filed: Apr. 9, 1984

[51] Int. Cl.$^4$ .............................................. L07C 27/06
[52] U.S. Cl. .................................... 518/700; 518/715
[58] Field of Search ............................... 518/700, 715

[56] References Cited

U.S. PATENT DOCUMENTS 4,366,259  12/1982  Knifton et al. ..................... 518/200

FOREIGN PATENT DOCUMENTS

| 033425 | 8/1981 | European Pat. Off. ............ 518/700 |
| 0098031 | 1/1984 | European Pat. Off. . |
| 57-130937 | 8/1982 | Japan . |
| 58-67641 | 4/1983 | Japan . |

*Primary Examiner*—Howard T. Mars
*Attorney, Agent, or Firm*—Kenneth D. Tremain

[57] ABSTRACT

A process for preparing acetic acid and acetates comprising reacting carbon monoxide with hydrogen in the presence of a catalytically effective amount of the catalyst system comprising a ruthenium compound, a cobalt compound, and an alkali metal halide activator.

13 Claims, No Drawings

PROCESS FOR THE PRODUCTION OF ACETIC ACID FROM SYNTHESIS GAS

BACKGROUND OF THE INVENTION

1. Field of the Invention

This invention concerns a process for the preparation of acetic acid by the direct conversion of carbon monoxide and hydrogen (synthesis gas or syngas) by a specific catalyst system accompanied by a minimum of solvent hydrolysis.

2. Description of the Prior Art

Acetic acid has an important place in the organic chemical industry in that it is the substrate for the production of, amongst others, vinyl acetate which is used in the manufacture of polymers, numerous amino acids, and dietary supplements such as glutamic acid, citric acid and lysine. The commercial processes leading to the production of acetic acid include acetaldehyde oxidation, liquid phase hydrocarbon oxidation, and methanol carbonylation.

With regard to the conversion of syngas to acetic acid, the common current practice is a two-step process in which syngas is converted to methanol over a copper-zinc-aluminum oxide catalyst and the resulting methanol is then carbonylated in the presence of a homogeneous rhodium catalyst.

However, the ever-increasing scarcity of fuel has generated an urgency for the development of chemically more efficient routes to acetic acid which demand the least energy consumption.

A process involving the direct conversion of syngas to a mixture of acetic acid, ethanol and acetaldehyde over metallic rhodium is described in German Pat. No. 2,503,233 to U.C.C. While such a direct route eliminates the methanol formation step, there are several drawbacks to this process including the high cost and limited availability of rhodium, as well as a lack of selectivity to acetic acid.

U.S. Pat. No. 4,366,259 discloses a method for making acetic acid and propionic acid and their esters which comprises contacting a mixture of CO and $H_2$ with a catalyst system composed of a ruthenium-containing compound and a cobalt halide dispersed in a low melting quaternary phosphonium or ammonium salt at a temperature of at least about 150° C. and at a pressure of about 500 psig, or greater. Optionally, an organic iodide containing compound can be added to the catalyst combination in order to achieve improved selectivity to acetic acid. While selectivity to acetic acid can be improved with the use of the organic iodide compound, such selectivity needs further improvement.

SUMMARY OF THE INVENTION

It is an object of the present invention to improve current methods for producing acetic acid to provide a process for very selectively producing acetic acid from syngas in good yields.

To achieve the objects in accordance with the invention, it has now been discovered that acetic acid and its esters with a lesser amount of alcohols and methane, can be readily and conveniently prepared by the liquid phase reaction of synthesis gas in the presence of a catalytically effective amount of a homogeneous catalyst system comprising a ruthenium compound, a cobalt compound, and an alkali metal halide activator.

DESCRIPTION OF THE PREFERRED EMBODIMENTS

The homogeneous catalysis can be carried out on a batch or continuous basis, the latter being more readily suitable to low-cost operation.

The relative amounts of hydrogen and carbon monoxide which may be initially present in the syngas mixture are variable. In general, the mole ratio of $H_2:CO$ is in the range of from about 10:1 to 1:10 preferably 5:1 to 1:5. Particularly in continuous operations, the syngas mixture may be used in conjuction with up to 50% by volume of one or more gases which do not hamper the instant process.

The present invention most readily occurs in the liquid phase and at elevated temperatures and pressures. Temperatures can be varied from about 150° C. to about 300° C., but the temperature required for advantageous results is about 200° C. Pressures ranging from about 500 psig to almost any pressure attainable with production apparatus can be used. Since extremely high pressure apparatus is quite expensive, pressures of about 1000 to about 7000 psig are suggested. Desirably, the pressure should be in the range of from about 4500 psig to about 5600 psig, particularly when employing the aforesaid temperature range.

Catalyst systems within the scope of the present invention contain a ruthenium compound, a cobalt compound, and a halide activator.

Illustrative of suitable ruthenium compounds are $Ru_3(CO)_{12}$, $RuCl_3$, $RuBr_3$, $RuI_3$, $(C_5H_5)_2Ru$, $H_4Ru_4(CO)_{12}$, $LiRuCl_3(CO)_3$, $[Ru(C_5Me_5)(CO)_2]_2$, $[RuCl_2(C_6Me_6)CO]_2$, $(C_5Me_5)Ru(CO)_2SnCl_3$, $(C_5Me_5)_2Ru_2(CO)_4SnCl_2$, $[RnCl_2(CO)_3]_2$, $RuCl_3(CO)_3$ anion and the like; ruthenium dichloride tricarbonyl dimer and ruthenium trichloride tricarbonyl anion being especially preferred. In the instance where the ruthenium compound chosen has a net charge, it is acceptable to balance said charge with any known positive counterion, e.g., bis(triphenylphosphine)iminium (PPN).

A wide variety of cobalt compounds are suitable in the practice of this invention, including $Co_4(CO)_{12}$, $CoBr_2$, $CoCl_2$, $CoI_2$, $PPNCo(CO)_4$, $NaCo(CO)_4$, $(C_5H_5)_2Co$, $Co(CO)_3NO$, $[Ph_3PCo(CO)_3]_2$, $Co(OAc)_2 \cdot 4H_2O$, and $Co_2(CO)_8$. Cobalt acetate and dicobalt octacarbonyl are preferable.

The alkali metal halide activator can be any alkali metal halide, preferably lithium iodide, lithium bromide, and lithium chloride or a combination thereof. Since the alkali metal halide activator is not a solvent, the catalyst system further comprises a suitable solvent, preferably for providing homogeneous liquid phase catalysis.

Aprotic organic amides have been found particularly useful in this regard and include N-substituted amides in which the hydrogens of the amido nitrogen are substituted by a hydrocarbon group preferably containing not more than 8 carbon atoms, e.g., 1-methyl-pyrrolidin-2-one, N,N-dimethylacetamide, N,N-diethylacetamide, N-methylpiperidone, 1,5-dimethylpyrrolidin-2-one, 1-benzylpyrrolidin-2-one, N,N-dimethylpropionamide, hexamethylphosphoric triamide and similar such liquid amides, cyclic amides, i.e., in which the amido group is part of a ring structure such as in pyrrolidinones and piperidones; acylated cyclic amines, such as N-acyl piperidines, pyrroles, pyrrolidines, piperazines, morpholines, and the like, as well as acyclic amides, i.e., wherein the amido group is not part of a ring structure as in acetamides, formamides, propionamides, caproamides and the like. The most preferred amide solvents include the N-substituted cyclic amides, N-methyl pyrrolidone (NMP) being especially preferred.

The amides are preferred solvents since their use results in the highest yields of product in present experience. Other solvents, usually aprotic, can be used but the yields are substantially less than obtained with the preferred amide solvents. Such solvents include, for example, cyclic ethers such as tetrahydrofuran, dioxane and tetrahydropyran; ethers such as diethyl ether, 1,2-dimethoxybenzene; alkyl ethers of alkylene glycols and polyalkylene glycols, e.g., methyl ethers of ethylene glycol, propylene glycol and di-, tri- and tetraethylene glycols; ketones such as acetone, methyl isobutyl ketone, and cyclohexanone; esters, such as ethyl acetate, ethyl propionate and methyl laurate; and alkanols, such as methanol, ethanol, propanol, 2-ethylhexanol and the like; tetramethylurea; γ-butyrolactone; tertiary amines such as N-methylpyrrolidine; and mixtures thereof.

Of course, mixtures of the solvents can be used, e.g., amide solvent with other solvents. Further, the amount of solvent is not critical in the instant invention, any amount sufficient to dissolve the chosen ruthenium-cobalt-alkali metal halide catalyst being useful herein.

Any water formed in side reactions tends to react with carbon monoxide to form $CO_2$ and hydrogen (water gas shift).

The quantity of ruthenium-cobalt-halide catalyst employed herein can vary over fairly wide limits and the level of catalyst selected will be such as to provide the desired products in reasonable yields. At least a catalytically effective amount of catalyst should be used, of course. A catalyst system wherein the concentration of ruthenium expressed as metal is between about 0.004M to 0.5M, preferably about 0.008M to 0.2M, and the concentration of cobalt expressed as metal is between about 0.002M to 0.5M, preferably about 0.004M to 0.2M, is generally desirable in the practice of this invention. The upper concentration is governed by a variety of factors including catalyst cost, partial pressures of carbon monoxide and hydrogen, operating temperatures and choice of solvent.

In addition, the stoichiometric ratios of ruthenium:cobalt and (ruthenium and cobalt): alkali metal halide (in the halide activator) may vary over a wide range. For example, said stoichiometric ratio of ruthenium:cobalt can vary from about 10:1 to about 1:10. The preferred range is from about 5:1 to about 1:5. Total (ruthenium and cobalt) to alkali metal halide activator molar ratio may vary from about 1:1 to about 1:100, most preferably from about 1:3 to about 1:50.

The following examples serve to illustrate specific embodiments of the present invention and to provide comparative data for discussion and further understanding of the invention and are not intended to limit the scope thereof.

The results of these examples, including selectivity, acetate productivity rate, and CO conversion rate are summarized in Table I.

TABLE I

Ru—Co Catalyzed Direct Syngas Reaction to Acetic Acid[1]

| Example | Ruthenium Concentration Molar[2] | Cobalt Concentration Molar[3] | Additive | Molar | HOAc | MeOAc | EtOAc | MeOH | EtOH | n-PrOH | CH4 | Moles Acetate/ L. Soln/hr | Mole CO converted/ L. Soln/Hr.[4] |
|---|---|---|---|---|---|---|---|---|---|---|---|---|---|
| 1[5] | 0 | .019 | LiBr | 1.2 | tr. | tr. | 0 | tr. | tr. | 0 | 0 | tr. | tr. |
| 2 | .020 | 0 | " | " | tr. | 0 | 3 | 32 | 34 | 6 | 25 | .03 | 4.4 |
| 3 | .020 | .016 | " | " | 88 | tr. | 5 | 2 | 4 | .2 | 0 | 1.1 | 2.4 |
| 4 | .0039 | .016 | " | " | tr. | tr. | tr. | tr. | tr. | 0 | 0 | tr. | tr. |
| 5 | .020 | .0041 | " | " | 50 | 4 | 17 | 6 | 14 | 2 | 7 | .66 | 2.1 |
| 6 | 0 | .016 | LiI | .44 | tr. | tr. | 0 | 0 | 0 | 0 | 0 | tr. | tr. |
| 7 | .020 | 0 | LiI | .30 | tr. | 0 | tr. | 39 | 28 | 3 | 28 | tr. | 3.6 |
| 8 | .020 | .016 | LiI | .30 | 41 | tr. | 17 | 6 | 15 | 4 | 16[6] | 1.2 | 4.7 |
|  |  |  | LiCl | 1.2 |  |  |  |  |  |  |  |  |  |
| 9 | .020 | .016 | (PPN)Cl | .18 | tr. | tr. | 4 | 74 | 21 | 1 | 0 | .02 | 1.9 |
| 10 | .020 | .016 | (PPN)Cl | .18 | tr. | tr. | 10 | 57 | 21 | 3 | 8 | .05 | 1.8 |
|  |  |  | LiBr | .03 |  |  |  |  |  |  |  |  |  |
| 11 | .019 | .016 | (PPN)Cl | .18 | 15 | 7 | 13 | 8 | 18 | 3 | 35 | .69 | 5.3 |
|  |  |  | LiBr | .58 |  |  |  |  |  |  |  |  |  |
| 12 | .020 | 0 | LiBr | .58 | 0 | 0 | 0 | 61 | 18 | 4 | 18 | 0 | 2.5 |
| 13 | .020 | .016 | 0 | 0 | 0 | tr. | 5 | 68 | 24 | 4 | 0 | .02 | 1.9 |
| 14 | .020 | .016 | LiBr | .58 | 25 | 12 | 27 | 5 | 14 | 3 | 15 | 1.6 | 7.1 |
| 15 | .020 | 0 | LiI | .30 | tr. | 0 | 1 | 53 | 28 | 2 | 16 | .01 | 2.0 |
| 16 | .020 | .016 | LiI | .44 | 62 | tr. | tr. | 17 | 17 | 0 | 4 | .48 | 1.5 |
| 17 | .020 | .016 | LiI | .30 | 78 | tr. | 7 | 6 | 6 | 2 | 0 | .86 | 2.5 |
|  |  |  | LiBr | .58 |  |  |  |  |  |  |  |  |  |
| 18 | .020 | 0 | Ni(acac)2 | .02 | 4 | tr. | 4 | 44 | 23 | 4 | 21 | .08 | 3.0 |
|  |  |  | LiBr | .58 |  |  |  |  |  |  |  |  |  |
| 19 | .020 | .016 | LiBr | .58 | 0 | tr. | tr. | tr. | tr. | 0 | 0 | tr. | tr. |
|  |  |  | Bu3P | .20 |  |  |  |  |  |  |  |  |  |
| 20[7] | .016 | .020 | LiBr | .58 | 10 | 6 | 0 | 74 | 9 | 0 | 0 | .15 | 2.0 |
|  |  |  | Bu3P | .02 |  |  |  |  |  |  |  |  |  |
| 21[7] | .019 | .019 | LiBr | .58 | 90 | .6 | 0 | 2 | 8 | 0 | 0 | .11 | .2 |
| 22[7] | .021 | .026 | LiBr | .38 | 16 | 3 | — | 64 | 10 | 0 | 6 | .03 | .3 |
|  |  |  | Bu3P | .02 |  |  |  |  |  |  |  |  |  |
| 23 | .020 | .016 | CsBr | .58 | 8 | 6 | 5 | 40 | 24 | 4 | 14 | .17 | 2.3 |
| 24[8] | .021 | .021 | LiBr | .40 | 86 | 5 | — | 4 | 5 | 0 | 0 | .46 | 1.0 |
| 25[9] | .20 | .16 | n-Bu4PBr | — | 32 | 11 | 24 | 8 | 13 | 0 | 12 | 5.4 | 21 |
| 26[9] | .10 | .085 | n-Bu4PBr | — | 51 | 5 | 26 | .4 | 5 | 1 | 12 | 3.3 | 10 |
| 27[10] | .012 | .011 | LiBr | .36 | 28 | 6 | 5 | 21 | 23 | 0 | 17 | .68 | 3.9 |
| 28[11] | .0081 | .0075 | LiI | .13 | 56 | 1 | — | 19 | 17 | 3 | 4 | .3 | 1.1 |
|  |  |  | LiI | .10 |  |  |  |  |  |  |  |  |  |
| 29[7] | .022 | .052 | LiBr | .42 | 96 | 0 | 0 | 4 | 0 | 0 | 0 | .2 | .4 |
| 30 | .020 | .016 | LiBr | .58 | 51 | 4 | — | 17 | 12 | 2 | 14 | .3 | 1.0 |
| 31[5] | .020 | .016 | LiBr | .58 | 39 | — | 8 | 5 | 14 | 2 | 32 | .5 | 2.4 |
| 32[12] | .017 | .024 | LiBr | .48 | 18 | 5 | 18 | 2 | 15 | 6 | 34 | .2 | 1.0 |

TABLE I-continued

Ru—Co Catalyzed Direct Syngas Reaction to Acetic Acid[1]

| Example | Ruthenium Concentration Molar[2] | Cobalt Concentration, Molar[3] | Additive, Molar | Selectivity, %[4] HOAc | MeOAc | EtOAc | MeOH | EtOH | n-PrOH | $CH_4$ | Moles Acetate/ L. Soln/hr | Mole CO converted/ L. Soln/Hr.[4] |
|---|---|---|---|---|---|---|---|---|---|---|---|---|
| 33[13] | .021 | .020 | LiBr .72 | 8 | 11 | tr. | 67 | 14 | 0 | 0 | .05 | .6 |

[1]N—Methylpyrrolidone solvent; 1.5:1 $H_2$:CO charged to 4500 psig at 20° C. (2000 psig for Examples 30, 31); two-hour reaction at 250° C.; 71 ml shaken reactors. Examples 22, 24, 27-29 run in 300 ml stirred reactor at constant pressure (2050 psig for Example 22, 5550 psig for Examples 24, 27-29).
[2]Examples 12-19 and 23 had $PPNRuCl_3(CO)_3$ as Ru—component. Example 32 had $(Ph_3P)_2RuCl_2(CO)_2$. All others had $[RuCl_2(CO)_3]_2$.
[3]Examples 20-22, 24, 26, 29, 32 had $Co_2(CO)_8$ as Co—component. All others had cobalt acetate.
[4]Based on CO in products other than $CO_2$.
[5]1:1 $H_2$:CO.
[6]Includes ethane.
[7]220° C.
[8]232° C., one-hour reaction.
[9]NMP deleted. n-Bu PBr served as molten salt solvent.
[10]Three-hour reaction at 235° C.
[11]One-hour reaction at 220-260° C.
[12]17-hour reaction.
[13]N—methylpyrrolidine solvent, 235° C.

EXAMPLES 1-32

Either a microreactor or a stirred reactor (each glass lined) was charged with catalyst, additive, and solvent components and sealed in an air free atmosphere. Microreactors were purged, then pressurized with syngas to the desired pressure (chamber temperature about 20° C.), then shaken at the desired temperature for two hours. For stirred reactor experiments, syngas was charged to the desired pressure and the reactor heated to reaction temperature. A continuous flow of gas was removed from the reactor (held at constant pressure) and collected for analysis. Liquid sampling was performed periodically.

The products obtained were analyzed by gas-liquid chromatography (GLC). Selectivities, carbon monoxide conversion rates, and acetate formation rates were determined. All experimental details and analysis results are contained in Table I.

DISCUSSION

A review of Table 1 reveals that the high selectivity to acetic acid is achieved by the use of the catalyst system according to the present invention which comprises catalytically effective amounts of ruthenium compound, cobalt compound, and an alkali metal halide activator. As is apparent from Table 1, the selectivity can be effected by the amount of catalyst component used as well as the type of component used according to the present invention. For example, Example 3 shows a selectivity of 88% for acetic acid when 0.020 M concentration of ruthenium compound are used., when for Example 4, where the same amount of cobalt compound and lithium bromide compound are used and only 0.0039 M concentration of ruthenium compound are used, only a trace amount of acetic acid is obtained.

The scope of the present invention is not limited by the description, examples and suggested uses herein, and modifications can be made without departing from the spirit of the invention. For example, the alkali metal activator can be a combination of lithium and cesium halides such as lithium bromide and cesium bromide in order to produce acetic acid in accordance with the invention. Thus, it is intended that the present invention cover the modifications and variations of this invention provided that they come within the scope of the appended claims and their equivalents.

What is claimed is:

1. A process for preparing acetic acid and acetates which comprises reacting carbon monoxide with hydrogen in the liquid phase at a pressure of at least about 500 psig and a temperature of from about 150° C. to about 300° C. in the presence of a catalytically effective amount of a catalyst system comprising a ruthenium compound, a cobalt compound and an alkali metal halide activator.

2. The process of claim 1 wherein the reaction is carried out at a pressure of from about 1000 psig to about 7000 psig.

3. The process of claim 1 wherein the reaction is carried out at a pressure of from about 4500 psig to about 5600 psig.

4. The process of claim 1 wherein the reaction is carried out at a temperature of from about 200° C. to about 300° C.

5. The process of claim 1 wherein the minimum concentration of ruthenium expressed as metal is between about 0.004M to 0.5M, and the minimum concentration of cobalt expressed as metal is about 0.002M to 0.5M.

6. The process of claim 1 wherein the minimum concentration of ruthenium expressed as metal is between about 0.008M and 0.2M and the minimum concentration of cobalt expressed as metal is between about 0.004M to 0.2M.

7. The process of claim 1 wherein the ruthenium compound is a ruthenium carbonyl halide complex.

8. The process of claim 7 wherein the ruthenium carbonyl halide complex is selected from the group consisting of ruthenium dichloride tricarbonyl dimer and bis(triphenylphosphine)imimium ruthenium trichloride tricarbonyl.

9. The process of claim 1 wherein the cobalt compound is selected from the group consisting of cobalt acetate and dicobalt octacarbonyl.

10. The process of claim 1 wherein the alkali metal halide activator is at least one alkali metal halide salt and further comprises an aprotic organic amide solvent.

11. The process of claim 10 wherein at least one halide salt is selected from the group consisting of lithium bromide, lithium iodide, and lithium chloride.

12. The process of claim 10 wherein the aprotic organic amide solvent is an N-substituted amide.

13. The process of claim 12 wherein the N-substituted amide is N-methyl-2-pyrrolidone.

* * * * *